United States Patent
Sieth et al.

(10) Patent No.: US 7,329,338 B2
(45) Date of Patent: Feb. 12, 2008

(54) CONDUCTIVITY SENSOR FOR AN ION EXCHANGE WATER SOFTENER

(75) Inventors: Kenneth J. Sieth, Delafield, WI (US); Mark J. Wittig, Franklin, WI (US)

(73) Assignee: General Electric Company, Schenectady, NY (US)

( * ) Notice: Subject to any disclaimer, the term of this patent is extended or adjusted under 35 U.S.C. 154(b) by 520 days.

(21) Appl. No.: 10/976,090

(22) Filed: Oct. 27, 2004

(65) Prior Publication Data

US 2006/0086648 A1    Apr. 27, 2006

(51) Int. Cl.
*B01D 17/12* (2006.01)
(52) U.S. Cl. ............... 210/96.1; 73/866.5; 210/190; 210/269; 324/439; 324/450
(58) Field of Classification Search .......... 210/85, 210/96.1, 138–140, 190, 191, 263, 269, 270, 210/662; 73/866.5; 324/425, 439, 445, 324/446, 450

See application file for complete search history.

(56) References Cited

U.S. PATENT DOCUMENTS

| | | | |
|---|---|---|---|
| 3,246,759 A | * | 4/1966 | Matalon ............... 210/96.1 |
| 3,574,330 A | * | 4/1971 | Prosser ............... 210/96.1 |
| 4,158,628 A | | 6/1979 | Fleckensteim |
| 4,237,538 A | | 12/1980 | Le Dall |
| 4,275,448 A | | 6/1981 | Le Dall |
| 4,299,698 A | | 11/1981 | Rak et al. |
| 4,320,010 A | | 3/1982 | Tucci et al. |
| 4,385,357 A | | 5/1983 | Davis et al. |
| 4,385,992 A | | 5/1983 | Clauer et al. |
| 4,469,602 A | | 9/1984 | Seal |
| 4,491,798 A | | 1/1985 | Palmer et al. |
| 4,568,465 A | | 2/1986 | Davis et al. |
| 4,659,463 A | | 4/1987 | Chandler et al. |
| 4,668,386 A | | 5/1987 | Seal et al. |
| 4,737,275 A | | 4/1988 | Franks |
| 4,814,090 A | | 3/1989 | Kunz et al. |
| 4,987,409 A | | 1/1991 | Jackson |
| 5,022,994 A | | 6/1991 | Avery et al. |
| 5,061,372 A | | 10/1991 | Rak |
| 5,132,669 A | | 7/1992 | Jackson |
| 5,147,531 A | | 9/1992 | Dougal |
| 5,234,601 A | * | 8/1993 | Janke et al. ............... 210/662 |
| 5,310,488 A | | 5/1994 | Hansen et al. |
| 5,363,087 A | | 11/1994 | Johannsen et al. |
| 5,480,555 A | | 1/1996 | Member |
| 5,699,272 A | | 12/1997 | Zabinski |
| 5,751,598 A | | 5/1998 | Zabinski et al. |
| 6,032,821 A | * | 3/2000 | Martin et al. ............... 220/565 |

(Continued)

*Primary Examiner*—Joseph Drodge
(74) *Attorney, Agent, or Firm*—George E. Haas; Quarles & Brady

(57) ABSTRACT

A water treatment system includes a tank that contains a particle bed for removing minerals from water flowing through the tank. The regeneration of the particle bed is conducted in response to measuring its conductivity. A probe is provided for that measuring. That probe has a sleeve with a tubular portion for extending through and engaging a wall of the tank. A probe body is removably received within an aperture of the sleeve and includes a pair of electrodes that project inside the tank. A retainer that secures the probe body within the sleeve. Different mechanisms are provided for securing the sleeve to the tank depending upon the particular materials used to fabricate the tank.

20 Claims, 2 Drawing Sheets

U.S. PATENT DOCUMENTS

| | | |
|---|---|---|
| 6,235,200 B1 | 5/2001 | Mace |
| 6,293,298 B1 | 9/2001 | Brane et al. |
| 6,436,293 B1 | 8/2002 | Carli |
| 6,491,181 B1 | 12/2002 | Martin et al. |
| 6,527,958 B1 | 3/2003 | Carli et al. |
| 6,696,966 B2 | 2/2004 | Bearak |

* cited by examiner

CONDUCTIVITY SENSOR FOR AN ION EXCHANGE WATER SOFTENER

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to apparatus for softening water; and particularly to systems for controlling regeneration of the resin in a water softening apparatus.

It is quite common for water drawn from a well to be considered "hard" in that it contains di-positive and sometimes tri-positive ions which have leached from mineral deposits in the earth. Such ions form insoluble salts with common detergents and soaps producing precipitates that increase the quantity of detergent or soap required for cleaning purposes. When hard water is used in boilers, evaporation results in the precipitation of insoluble residues that tend to accumulate as scale.

It is common practice to install a water softener in the plumbing system of a building that is supplied with hard water. The most common kind of water softener is an ion exchange apparatus that has a tank which holds a bed of resin through which the hard water flows to remove undesirable minerals and other impurities. Binding sites in the resin bed initially contain positive ions, commonly unipositive sodium or potassium ions. As hard water enters the resin, competition for the binding sites occurs. The di-positive and tri-positive ions in the hard water are favored due to their higher charge densities and displace the uni-positive ions. Two or three unipositive ions are displaced for each di-positive or tri-positive ion, respectively.

The capacity of the resin bed to absorb minerals and impurities is finite and eventually ceases to soften the water when a large percentage of the sites become occupied by the di-positive and tri-positive ions. When this occurs, it becomes necessary to recharge or regenerate the resin bed by flushing it with a regenerant, typically a solution of sodium chloride or potassium chloride. The concentration of uni-positive ions in the regenerant is sufficiently high to offset the unfavorable electrostatic competition and the binding sites are recovered by unipositive ions. The interval of time between regeneration periods during which water softening takes place is referred to as a "service cycle."

Regeneration of early types of water softeners was affected manually only after it was discovered that the treatment capacity of the resin bed has been exceeded and the water flowing there through is no longer "soft." In an effort to eliminate the need for manual regeneration, water softener control systems were provided with a mechanical clock which initiated water softener regeneration on a periodic basis. The frequency of such regeneration was set in accordance to the known capacity of the resin bed and the anticipated daily usage of soft water. Although mechanical clock-type water softener controllers alleviated the need for manually regenerating the resin bed, such controllers are subject to the disadvantage that regeneration at fixed intervals may occur too often or not often enough depending upon water usage. Regenerating the water softener resin bed when sufficient capacity to treat water still exists wastes the regenerant and the water used in regeneration. Conversely, failure to regenerate the water softener after the resin bed capacity has diminished to a point below that required to treat hard water may result in hard water leaving the water softener.

In an effort to better regulate the frequency of water softener regeneration, demand-type water softener controls have been developed which determine the remaining capacity of the resin bed to soften water. One type of such an improved control system is disclosed in U.S. Pat. No. 4,426,294 in which a flow meter measures the volume of water being treated and regenerates the resin bed when a specified volume of water has flowed through the softener since the previous regeneration. While this type of system is adequate in many installations, municipal systems alternately may draw water from several wells which contain water having different degrees of hardness. In that case, the exhaustion of the resin bed is not a direct function of the volume of water which has been treated since the previous regeneration.

Other types of control systems were developed which detect the exhaustion of the resin bed directly. For example, U.S. Pat. No. 5,234,601 utilizes electrodes to measure the electrical conductivity of the resin bed at two spaced apart locations. The ratio of the conductivity measurements, along with the minimum and maximum ratio values that occurred since the previous resin bed regeneration, are used to determine a probability of resin bed exhaustion and this trigger regeneration.

In this conductivity based system, wires extend from the controller through the opening at the top of the resin tank through which the water also entered and exited the tank. Thus the wires and their connection to the sensing electrodes were exposed to the water and to the brine solution used during regeneration. That exposure often had a deleterious effect on the wires and the electrode connection.

The present inventors proposed solving this problem by extending the electrodes through the sidewall of the resin tank, however this approach was complicated by the curved sidewall of the tank. In addition, some resin tanks have a polyethylene liner within a fiberglass outer shell and the liner is not adhered to the shell which makes a water tight connection between the electrode and the tank very difficult.

Therefore, it is desirable to provide a water tight assembly for inserting the conductivity sensing electrodes through the sidewall of the resin tank in a water tight manner.

SUMMARY OF THE INVENTION

A water treatment system includes a tank that contains a particle bed which removes minerals from water that flows through the tank. A probe is provided to measure conductivity of the resin bed to provide a signal that is used to determine when the particle bed requires regeneration.

The probe comprises a sleeve with a tubular portion for extending through and engaging a wall of the tank. An aperture extends through the sleeve. The sleeve may have one of several forms so as to be securable to tanks of different construction. One embodiment of the sleeve is designed for tanks with a liner made of a non-bondable material that can not be attached to the inner surface of a rigid outer shell of the tank. This particular sleeve has an outwardly projecting flange at an interior end of a tubular portion that extends through an opening in the tank wall. The tubular portion has external screw threads that are engage by a nut outside the tank to secure the sleeve in the opening.

Another embodiment of the sleeve is designed for use on tanks where the liner is made of a material that is bonded to the inner surface of the rigid outer shell. Here, external screw threads on the tubular portion engage threads on an opening through a wall of the rigid outer shell to secure the sleeve on the tank.

A probe body is removably received within the aperture of the sleeve and has at least one electrode projecting into contact material inside the tank. A retainer that secures the probe body within the sleeve.

DESCRIPTION OF THE OF THE DRAWINGS

DETAILED DESCRIPTION OF THE INVENTION

Figure 1:
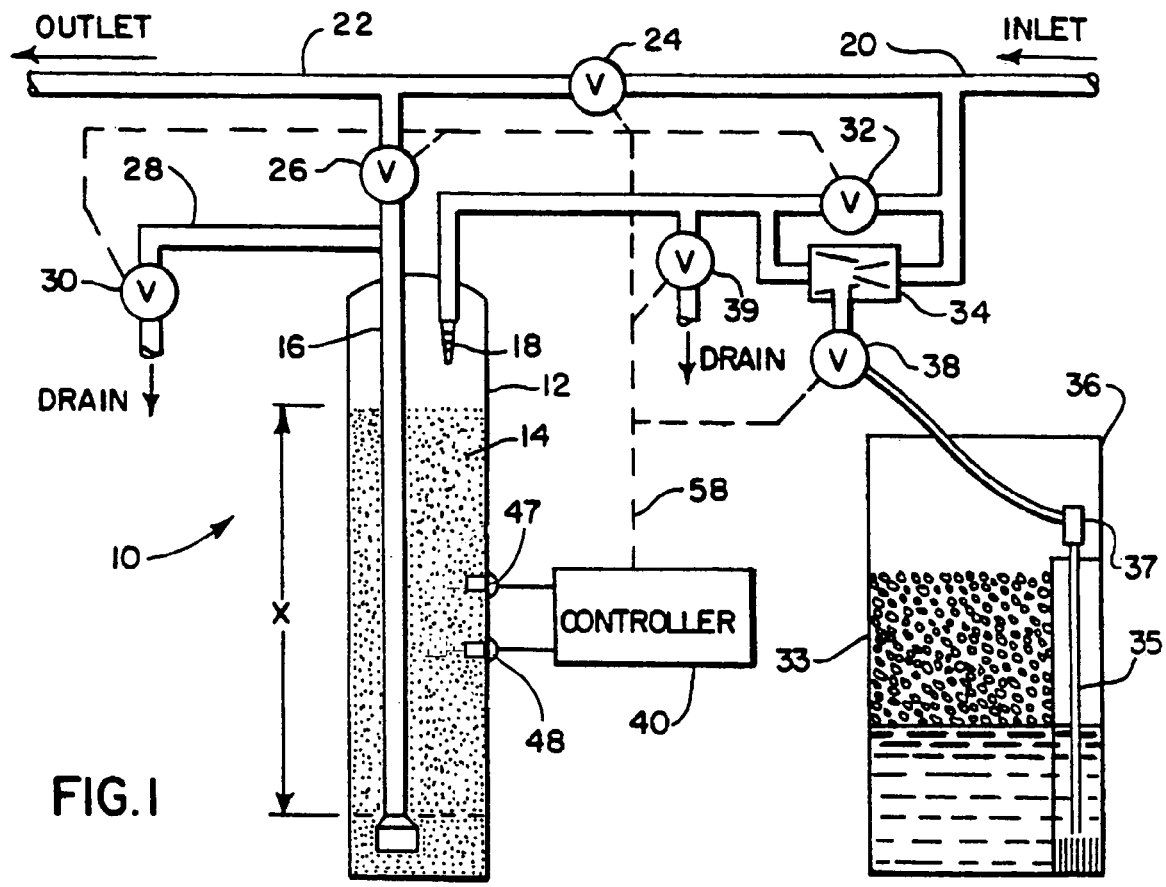
FIG. 1 is a schematic view of a system for regenerating a water softener according to the present invention.

Referring initially to FIG. 1, a water softener 10 includes a softening tank 12 which contains a bed 14 of ion exchange resin particles. An outlet conduit 16 extends through the bed 14 from a point adjacent the bottom of the bed. An inlet conduit 18 extends into the water softener tank 12 and has a discharge opening above the level of the resin bed 14. Hard water is delivered through an inlet line 20 and treated water is delivered through a service line 22. The inlet line 20 and the service line 22 are connected through a normally closed first service valve 24. A normally open second service valve 26 is interposed between the outlet conduit 16 and the service line 22. A drain line 28 containing a normally closed first drain valve 30 also extends from the outlet conduit 16.

Hard water ordinarily is delivered to the inlet conduit 18 through a normally open service inlet valve 32. Alternatively, hard water entering the inlet line 20 can pass through an injector 34 to draw a regenerant solution from a brine tank 36 when a brine inlet valve 38 is opened and when the service inlet valve 32 is closed. The brine tank 36 contains a common salt 33, such as a sodium chloride or potassium chloride. The withdrawn brine is delivered through line 35 to the inlet conduit 18 of the softener. The inlet conduit 18 also is connectable to a drain through a normally closed second drain valve 39.

During service operation, the drain valves 30 and 39, the first service valve 24 and the brine inlet valve 38 are all closed. In this mode of operation, the second service valve 26 and the service inlet valve 32 are open allowing hard water to flow from the inlet line 20 through the inlet conduit 18 onto the top of the resin bed 14. The water passes through the bed 14 and treated water is withdrawn from the bottom of the bed 14 through outlet conduit 16 and into the service line 22.

The resin bed 14 eventually becomes exhausted and no longer is capable of softening the water. A typical resin bed regeneration process commences with a backwash step. In this step, a controller 40 closes the service inlet valve 32 and the brine inlet valve 38, while opening the first service valve 24 and the second drain valve 39. Hard water from the inlet line 20 feeds through the outlet conduit 16 and upwards through the resin bed 14 finally exiting through the inlet conduit 18 and the now open second drain valve 39. Water continues to be supplied to the service line 22 at this time even though it is not being treated.

The backwash step is followed by a brining and rinsing. For this operation, the second service valve 26 and the second drain valve 39 are closed while the brine inlet valve 38 and the first drain valve 30 are opened. In this state, hard water is forced through the injector 34 and brine is withdrawn from the tank 36 through a brine line 35. The withdrawn brine is discharged into the softener tank 12 through inlet conduit 18. The brine passes through the resin bed 14 and drains through the outlet conduit 16 and the now open first drain valve 30. The concentrated brine solution replaces the di-positive and tri-positive ions in the resin with unipositive ions recharging the bed. When the contents of the brine tank 12 have been exhausted, an air check valve 37 closes to prevent air from being injected into the system and water will continue to flow through the injector 34 free of brine. This water propels the brine solution from the tank and then rinses the bed 14 to remove residual brine. Untreated water will be supplied to the service line 22 through the open first service valve 24 during this stage of operation.

During the next stage of operation, the brine tank 36 is refilled and the softener resin bed 14 is purged. This is accomplished by opening the service inlet valve 32 and the second service valve 26. Hard water then can enter the brine tank 36 through the open brine valve 38 and can enter the tank 12 through the inlet conduit 18. Water passing through the resin bed 14 exits via the open drain valve 30. The apparatus is returned to a service condition by closing the first service valve 24, the first drain valve 30 and the brine inlet valve 38.

Figure 2:
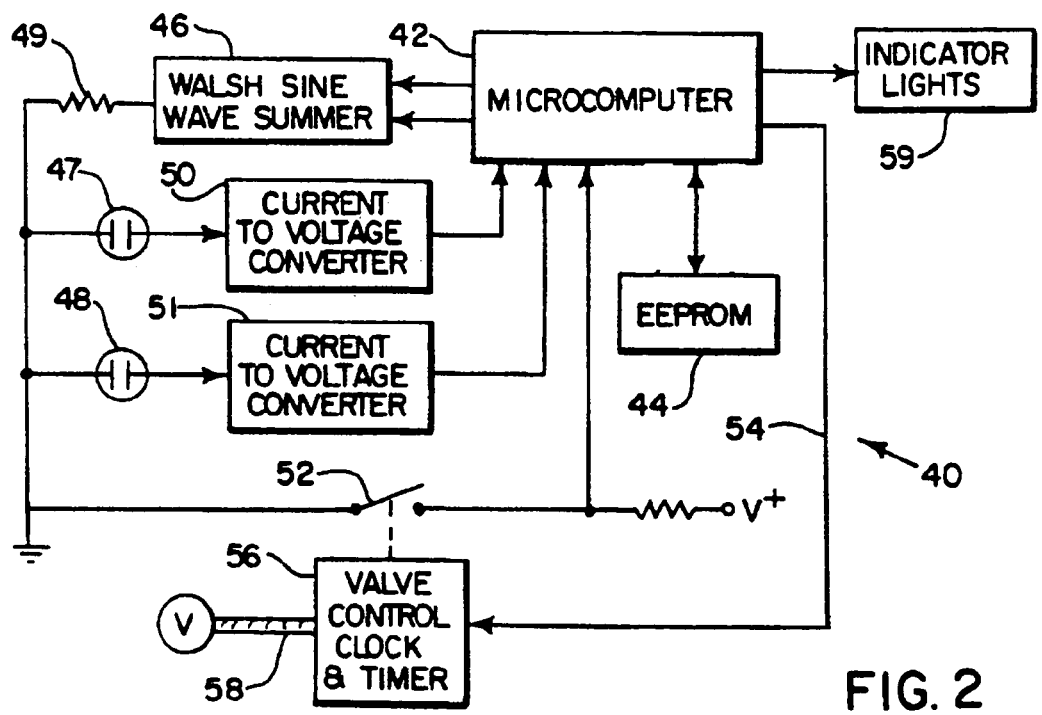
FIG. 2 is a schematic block diagram of the controller in FIG. 1.

Referring to FIG. 2, the controller 40 which operates the various valves illustrated in FIG. 1 is built around a microcomputer 42 which has internal analog-to-digital converters, memory, and clock circuits. An electrically erasable programmable read only memory (EEPROM) 44 is connected to the microcomputer 42 for the storage and retrieval of data. Outputs of the microcomputer 42 are connected to a Walsh sine wave summer 46 as described in an article entitled "Walsh Functions: A Digital Fourier Series" which appeared in Byte Magazine September 1977, pages 190-198, which is incorporated by reference herein. The output of the Walsh sine wave summer 46 is low pass filtered to remove high order harmonics leaving an essentially pure sine wave at a frequency of approximately 1,000 Hz. with an amplitude of approximately 100 mv-pk. The low excitation voltage is selected to prevent chemical reduction or oxidation from occurring at electrodes in the resin bed. A relatively high excitation frequency was selected to reduce the electrode double layer capacitance.

The output signal from the Walsh sine wave summer 46 is applied to common electrodes of two conductivity probes 47 and 48 that extend into the resin bed 14. The lower conductivity probe 48 is located at approximately thirty-eight percent of the effective height (X) of the bed which is the distance between the uppermost inlet opening at the bottom of outlet conduit 16 and the top of the resin bed. The position was chosen so that the lower conductivity probe 48 produces a indication of a conductivity change when approximately twenty percent of the capacity of the resin bed remains to treat water. The upper conductivity probe 47 is positioned in the resin bed approximately six inches above the lower conductivity probe 48.

Figure 3:
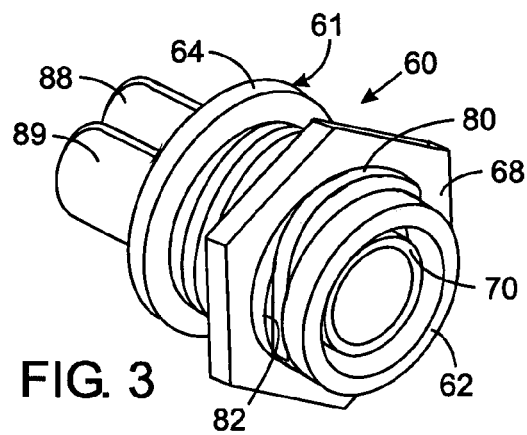
FIG. 3 is an isometric view of a conductivity probe that is used with the controller in FIG. 2.
Figure 4:
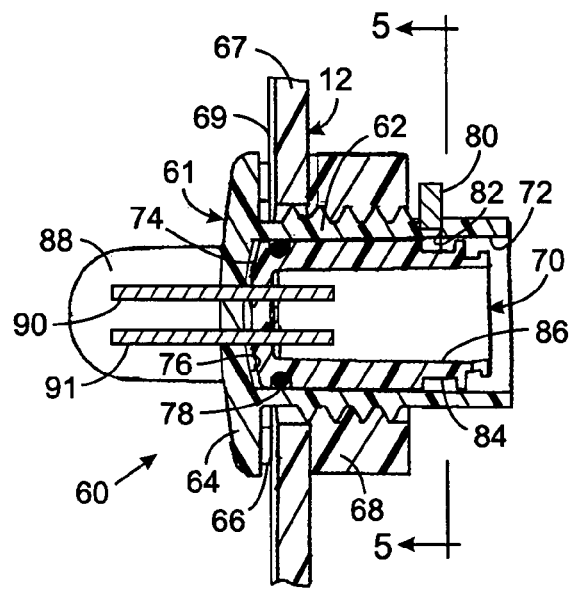
FIG. 4 is a cross section view through the conductivity probe of FIG. 3.

FIGS. 3 and 4 illustrate a first embodiment of a sensor probe 60 that can be used as the upper and lower conductivity probes 47 and 48 in FIG. 1. The sensor probe 60 has a sleeve 61 comprising a tubular section 62 with exterior thread and an outwardly projecting flange 64 at one end of the tubular section. The sleeve 61 extends through an aperture in the sidewall of the water softener tank 12 with the flange 64 compressing an annular rubber seal 66 against the inner surface of the tank 12 to provide a water tight seal. This sensor probe 60 is intended for use with a tank 12 having a fiberglass or steel outer body 67 with an polyethylene inner liner 69. Polyethylene and similar non-bondable materials form an inner liner 69 that is not bonded to the rigid outer body 67, nor can the probe sleeve 61 be adhered or otherwise bonded to these inner liners. As a result, the probe 60 has a flange 64 and the annular rubber seal 66 that provides a water tight abutment between the probe components and the inside surface of the tank 12. The probe 60 is held in place by a hexagonal nut 68 which is threaded onto the exterior of the tubular section 62 until it abuts the outer surface of the tank 12.

Figure 5:
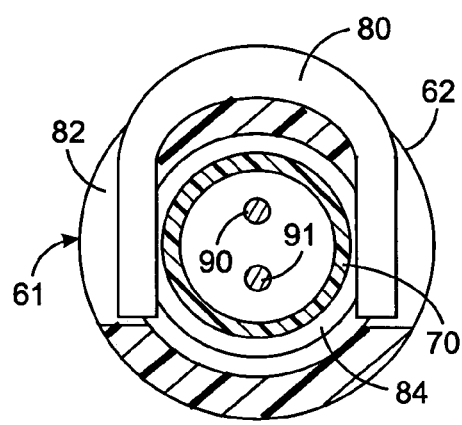
FIG. 5 is a cross section view along line 5-5 in FIG. 4.

A sensor body 70 is inserted from outside the tank into a central aperture 72 in the sleeve's tubular section 62. An annular exterior groove near an interior end 74 of the sensor body 70 contains an O-ring 78 to establish a water tight seal between the sensor body 70 and the sleeve 61. The sensor body 70 is held within the sleeve 61 by a U-shaped retaining clip 80 which slides within grooves 82 on opposite sides of the tubular section 62 of the sleeve, as also shown in FIG. 5. The side legs of the retaining clip 80 extend through the sleeve grooves 82 and enter an annular notch 84 around the outside of the sensor body 70. The engagement of the retaining clip 80 with the sleeve 61 and the groove 82 of the sensor body 70 holds the sensor body against the interior rib 76 of the sleeve.

A pair of walls 88 and 89 project outwardly from the interior end 74 of the sensor body 70 into the resin bed 14 inside the water softener tank 12. A pair of electrodes 90 and 91 project through the wall at the interior end 74 of the sensor body 70. When the sensor body 70 in inserted into the sleeve 61, each electrode 90 and 91 extends through a separate small aperture in the interior end wall 76 of the sleeve's central aperture 72. Those small apertures permit the sensor body 70 to be replaced with minimal loss of water from the tank 12. The electrodes 91 and 92 are fabricated of gold plated, stainless steel, for example. The stainless steel of the electrode structure resists corrosion, while the gold plating makes the surface chemically inert. However, the gold resists wetting by the water within the tank 12. In order to improve the wetting, a sleeve of an ion exchange material, such as Nafion (trademark of E.I. du Pont de Neumours & Co., Inc.) is inserted over each electrode 91 and 92. The sleeve "wets" the hydrophobic gold surface and keeps macro-molecules away from the electrode surface, thereby further stabilizing and preventing electrode contamination. The sleeve also protects the relatively soft gold surface from abrasion. Alternatively, graphite rods may be used as the electrodes and would not require gold plating.

The two electrodes 90 and 91 project into a cavity 86 in the sensor body. The cavity 86 is designed to receive a mating electrical connector (not shown) on the end of the cable that connects the sensor probe to the controller 40. That connector electrically engages ends of the electrodes 90 and 91.

Figure 6:
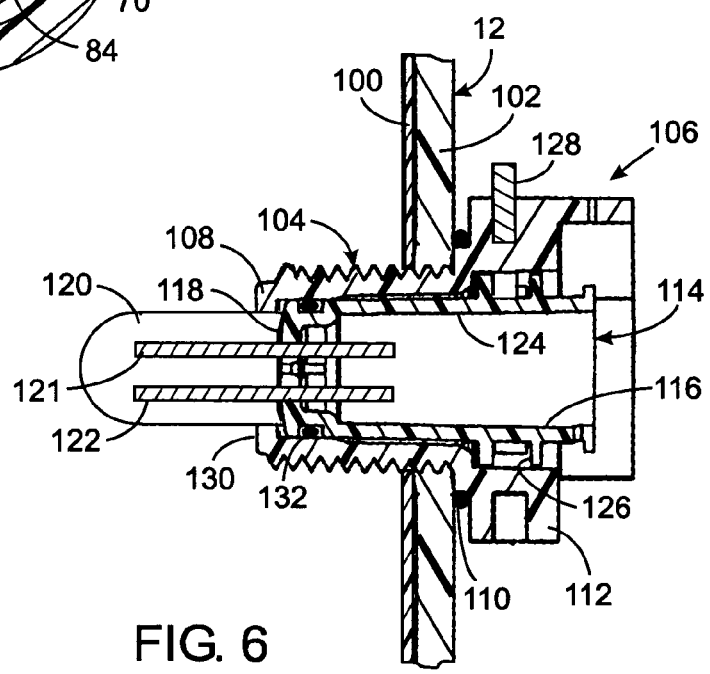
FIG. 6 is an cross sectional view of a second embodiment of a conductivity probe.

With reference to FIG. 6, some types of water softener tanks have a acrylonitrile butadiene styrene (ABS) liner 100 that is enclosed by and bonded to a fiberglass or steel outer body 102. The ABS liner 100 provides a water tight enclosure for the resin bed 14 and water being treated by the softener, while the outer body 102 provides a rigid structure for the softener tank 12. Because with this type of tank construction, the liner is bonded to the outer body to form an integrated structure, a sleeve 104 of the sensor 106 can be secured in a threaded aperture in the sidewall of the tank 12. Thus, the sleeve 104 has a cylindrical tubular portion 108 with external threads that engage threads cut in the outer body 102 of the tank 12. Upon inserting the sleeve 104 the threads are coated with an adhesive sealant which bonds the sleeve to the tank to form a water tight fitting. Alternatively, or in addition, a rubber sealing ring 110 can be provided between the outer surface of the tank 12 and a flange 112 at the outer end of the tubular portion 108 of the sleeve 104.

The sleeve 104 has an aperture there through for receiving the sensor body 114 which is structurally similar to the sensor body 70 in FIG. 4. Specifically, the sensor body 114 has an open end 116 adjacent the outer end of the sleeve 104 and a closed end 118 adjacent the sleeve's inner end. A pair of walls, only one of which, wall 120, is visible in the drawing, project from that end into the resin bed of the tank 12. A pair of electrodes 121 and 122 extend through the eludes end of the sensor body 114 between the two walls similar to that of the first sensor embodiment. The electrodes 121 and 122 extend into the cavity of the sensor body 124 for the purpose of making electrical connection to the cable from the controller 40. An annular groove 126 extends around the sensor body 124 to receive the legs of a U-shaped retaining clip 128 that is placed within notches in the sleeve 104. The engagement of the retaining clip 128 with the sensor body 114 held in abutment against the interior end 130 of the sleeve with the walls and the electrodes 121 and 122 extending through an aperture in that sleeve end 130. An O-ring 132 provides a seal between the exterior of the sensor body 114 and the interior surface of the sleeve 104.

Referring once again to FIGS. 1 and 2, the non-common electrode of each of the conductivity probes 47 and 48 is connected to a separate current-to-voltage converter 50 and 51, respectively. Each of these converters 50 and 51 transforms the magnitude of the current flowing through the associated probe 47 or 48 into a corresponding voltage level. The voltage outputs from the current to voltage converters 50 and 51 are applied to inputs of the microcomputer 42 which are connected to internal analog-to-digital (A/D) converters. The microcomputer 42 periodically enables each A/D converter in order to read the magnitude of the voltage produced by the associated current-to-voltage converter 50 and 51.

Another input line to the microcomputer 42 is connected to a service switch 52 which is closed whenever a regeneration of the water softener 10 is occurring. A set of indicator lamps 59 are activated by the microcomputer 42 as will be described, to provide indications to the user of events such as depletion of the salt in the brine tank 36 and probe failure. Other types of signaling devices, such as audible alarms, can be used.

The microcomputer 42 executes a control program which detects the currents flowing through the conductivity probes to determine when the resin bed 14 requires regeneration. The algorithm that the controller employs to determine when to regenerate the resin bed based on the conductivities is described in detail in U.S. Pat. No. 5,234,601. Whenever the control program from the microcomputer 42 determines that regeneration is required, a control signal is sent via line 54 to a conventional valve control clock and timer 56 as used in previous water softeners which regenerated the resin bed at a periodic interval and at a time of day (e.g. 2 a.m.) when water use is minimal. However, the valve control clock and timer 56 initiates regeneration of the resin bed 14 at that time of day only when a control signal is being received over line 54. If these conditions are met, the valve control clock and timer 56 rotates a cam shaft 58 which opens and closes the different valves illustrated in FIG. 1 in the sequence previously described to regenerate the resin bed.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

What is claimed is:

1. In a water treatment system having a tank containing a particle bed for removing minerals from water flowing through the tank and a system for regenerating the particle bed, a probe for measuring conductivity within the tank and comprising:
    a sleeve having a tubular portion for extending through and engaging a wall of the tank, the sleeve having an aperture there through;
    a probe body removably received within the aperture of the sleeve and including at least one electrode that projects outwardly therefrom to contact material inside the tank; and
    a retainer that secures the probe body within the sleeve.

2. The probe as recited in claim 1 wherein the sleeve has a stop formed within the aperture, the probe body abuts the stop, and the retainer maintains the probe body in contact with the stop.

3. The probe as recited in claim 1 wherein the probe body further comprises a pair of spaced apart walls projecting into the tank with the one electrode between the walls.

4. The probe as recited in claim 1 wherein the retainer comprises a retaining clip that is received within a first groove in the sleeve and in a second groove in the probe body.

5. The probe as recited in claim 1 wherein the sleeve has a tubular portion with a flange projecting outwardly therefrom.

6. The probe as recited in claim 5 wherein the tubular portion of the sleeve has external screw threads.

7. The probe as recited in claim 6 further comprising a nut that engages the external screw threads on the tubular portion of the sleeve.

8. The probe as recited in claim 6 wherein the external screw threads of the tubular portion of the sleeve engage screw threads in an aperture through the a wall of the tank.

9. A water treatment system comprising:
    a tank having a rigid outer shell, a liner within the shell, a water inlet conduit and a water outlet conduit;
    a particle bed within the liner of the tank for removing minerals from water;
    a probe sleeve having a tubular portion extending through the rigid outer shell and the liner of the tank, the sleeve having an aperture there through with stop formed therein;
    a probe body removably received within the aperture of the probe sleeve and abutting the stop, the probe body including a first electrode projecting inside the tank; and
    a retainer engaging both the probe sleeve and the probe body to maintain the probe body in abutment with the stop.

10. The water treatment system as recited in claim 9 wherein the probe body further comprises a pair of spaced apart walls projecting into the tank with the first electrode between the walls.

11. The water treatment system as recited in claim 10 wherein the probe body further comprises a second electrode projecting into the tank between the walls.

12. The water treatment system as recited in claim 9 wherein the retainer comprises a clip that is received within a first groove in the sleeve and a second groove in the probe body.

13. The water treatment system as recited in claim 9 wherein the liner is not bonded to the rigid outer shell.

14. The water treatment system as recited in claim 13 wherein the sleeve has a tubular portion with a flange projecting outwardly therefrom.

15. The water treatment system as recited in claim 14 wherein the tubular portion of the sleeve has external screw threads.

16. The water treatment system as recited in claim 15 further comprising a nut that engages the external screw threads on the tubular portion of the sleeve.

17. The water treatment system as recited in claim 13 wherein the outer shell is made of a material selected from the group consisting of steel and fiberglass.

18. The water treatment system as recited in claim 9 wherein the liner is bonded to the outer shell.

19. The water treatment system as recited in claim 9 wherein the tubular portion of the sleeve has external screw threads.

20. The water treatment system as recited in claim 19 wherein the external screw threads of the tubular portion of the sleeve engage screw threads in an aperture through the a wall of the tank.

* * * * *